United States Patent
Müh et al.

(10) Patent No.: US 7,507,850 B2
(45) Date of Patent: Mar. 24, 2009

(54) PREPARATION OF ORGANOSILANE ESTERS

(75) Inventors: Ekkehard Müh, Rheinfelden (DE); Hartwig Rauleder, Rheinfelden (DE); Harald Klein, Bessenbach (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/569,585

(22) PCT Filed: Apr. 4, 2005

(86) PCT No.: PCT/EP2005/051494

§ 371 (c)(1), (2), (4) Date: Jan. 10, 2007

(87) PCT Pub. No.: WO2005/118597

PCT Pub. Date: Dec. 15, 2005

(65) Prior Publication Data

US 2007/0249785 A1 Oct. 25, 2007

(30) Foreign Application Priority Data

May 26, 2004 (DE) .................. 10 2004 025 766

(51) Int. Cl.
C07F 7/04 (2006.01)
(52) U.S. Cl. .................. 556/471; 556/466; 556/445; 556/482; 524/866
(58) Field of Classification Search ................. 556/471, 556/466, 445, 482; 524/866
See application file for complete search history.

(56) References Cited

U.S. PATENT DOCUMENTS

| 4,876,337 | A |   | 10/1989 | Rauleder et al. |
| 5,248,803 | A | * | 9/1993 | Aoki et al. .................. 556/482 |
| 5,616,755 | A |   | 4/1997 | Seiler et al. |
| 5,698,726 | A |   | 12/1997 | Rauleder et al. |
| 5,786,493 | A |   | 7/1998 | Rauleder et al. |
| 5,852,206 | A |   | 12/1998 | Horn et al. |
| 5,939,575 | A |   | 8/1999 | Horn et al. |
| 6,150,551 | A | * | 11/2000 | Kropfgans et al. .......... 556/471 |
| 6,242,628 | B1 |   | 6/2001 | Kropfgans et al. |
| 6,423,858 | B1 |   | 7/2002 | Schwarz et al. |
| 6,750,361 | B2 |   | 6/2004 | Kropfgans et al. |
| 2002/0032354 | A1 |   | 3/2002 | Standke et al. |

FOREIGN PATENT DOCUMENTS

DE 199 41 283 5/2000

OTHER PUBLICATIONS

U.S. Appl. No. 11/569,585, filed Nov. 24, 2006, Mueh et al.

* cited by examiner

*Primary Examiner*—Daniel M Sullivan
*Assistant Examiner*—Chukwuma O Nwaonicha
(74) *Attorney, Agent, or Firm*—Oblon, Spivak, McClelland, Maier & Neustadt, P.C.

(57) ABSTRACT

The present invention relates to a specific process for preparing organosilane esters of the formula (I) and a composition comprising more than 98% by weight of organosilane esters of the formula (I) and less than 2.0% by weight of at least one hydrocarbon and to the use of such a composition as precursor for producing a layer or film having a dielectric constant of $1 < \kappa \leq 4$.

15 Claims, No Drawings

PREPARATION OF ORGANOSILANE ESTERS

The present invention relates to a specific process for preparing organosilane esters and to a composition comprising an organosilane ester and its use.

Organosilane esters are substances having a wide range of uses, e.g. in building protection compositions for waterproofing surfaces or for the crosslinking of structural elements, to name only a few.

With a view to their applications, the specification of the organosilane esters has to meet increasingly stringent requirements.

It has long been known that organohalosilanes can be esterified by means of usually excess alcohol or glycol. However, a frequently encountered problem is that the organosilane ester produced forms azeotropes with the esterifying alcohol or esterifying glycol, which makes isolation of the organosilane ester in satisfactory purity and on an economical scale extremely difficult or even impossible.

DE 197 55 597 A1 discloses a two-phase reaction in which nonpolar solvents which are immiscible with the esterifying alcohol in the esterification reaction bring advantages, in particular in respect of better removal of the hydrogen halide formed and a lower reaction temperature. Unfortunately, nothing is said about azeotropes or even avoidance of an azeotrope. Another disadvantage is that in this process it is only possible to use solvents which are immiscible with the alcohol used in the reaction under the reaction conditions which prevail. This means that the reactions are always phase boundary reactions which are disadvantageous compared to reactions in a homogeneous phase.

It is an object of the present invention to provide a product which is suitable for use in the electronics industry as precursor for producing a layer or film having a defined dielectric constant.

It has surprisingly been found that these problems can be solved in an advantageous fashion in the preparation of an organosilane ester from an organohalosilane and an alcohol or glycol by the targeted assistance of a synthesis or distillation auxiliary, in particular a hydrocarbon. The synthesis or distillation auxiliary added can be miscible, immiscible or partially miscible (miscibility gap) with the esterifying alcohol or esterifying glycol. The use of the synthesis or distillation auxiliary gives, after the reaction of organohalosilane and alcohol, a mixture comprising organosilane ester, alcohol and synthesis or distillation auxiliary which can, after targeted adjustment of the content of synthesis or distillation auxiliary, then be separated by distillation, with the synthesis auxiliary used substantially going into the gas phase under distillation conditions as a mixture with the alcohol present and giving a composition which comprises a particularly high proportion of organosilane ester and at least one hydrocarbon. Such a composition can advantageously be used for producing films. Such a film or layer has a dielectric constant of $1 < \kappa \leq 4$ and is thus advantageous, in particular, for electronic applications, e.g. in chip production.

The present invention accordingly provides a process for preparing organosilane esters of the general formula I $$R^1_a R^2_b R^3_c Si(OR^4)_{4-a-b-c} \quad (I),$$

where $R^1$=hydrogen, alkyl, preferably linear, branched, cyclic or halogen-substituted $C_1$-$C_{18}$-alkyl, particularly preferably n-propyl and isobutyl, alkenyl, preferably vinyl, aryl, preferably phenyl, $R^2$=hydrogen or alkyl, preferably linear, branched or cyclic $C_1$-$C_{18}$-alkyl, $R^3$=hydrogen or alkyl, preferably linear, branched or cyclic $C_1$-$C_{18}$-alkyl, and $R^4$=alkyl, preferably linear, branched or cyclic $C_1$-$C_6$-alkyl, aryl, preferably phenyl, or alkoxyalkyl, preferably 2-methoxyethyl, a, b and c can be identical or different and can each be 0, 1, 2 or 3, with the proviso that $(a+b+c) \leq 3$, by reacting an organohalosilane of the general formula II

$$R^1_a R^2_b R^3_c SiX_{4-a-b-c} \quad (II),$$

where $R^1$=hydrogen, alkyl, alkenyl or aryl, $R^2$=hydrogen or alkyl, $R^3$=hydrogen or alkyl and $R^4$=alkyl, aryl or alkoxyalkyl, X is fluorine, chlorine, bromine or iodine, a, b and c can be identical or different and can each be 0, 1, 2 or 3, with the proviso that $(a+b+c) \leq 3$, with an alcohol, including glycols, of the general formula III

$$R^4OH \quad (III)$$

where $R^4$=alkyl such as methyl, ethyl, propyl, isopropyl, butyl or isobutyl, aryl such as benzyl or phenyl, or alkoxyalkyl such as methoxyethyl, ethoxyethyl, propoxyethyl or butoxyethyl, wherein the halosilane, preferably chlorosilane, is reacted in the liquid phase with the alcohol of the formula III in the presence or absence of at least one synthesis auxiliary, i.e. solvent, diluent, entrainer or distillation auxiliary, hydrogen halide, preferably hydrogen chloride, is removed from the system, metal oxide, preferably as a solution in an alcohol corresponding to the alkoxy present, in particular alkali metal or alkaline earth metal alkoxide from the group consisting of Li, Na, K, Mg, is, if necessary, added to the reaction mixture to complete the esterification or to neutralize residual amounts of hydrogen halide still present and the metal salt formed is filtered off and an amount of synthesis auxiliary is added at least once before or during the subsequent work-up by distillation of the resulting, generally clear, preferably neutralized product mixture, with the amount added in each case being such that no azeotrope of one or more components of the product mixture and the organosilane ester of the formula I is formed during the preferably fractional distillation under the conditions which prevail.

The total amount of synthesis auxiliary added to the reaction and/or product mixture is appropriate such that the excess alcohol present in the product mixture can be substantially removed from the system by distillation as such or as an azeotrope of synthesis auxiliary and alcohol which has, in particular, a boiling point lower than that of the desired silane ester.

To set the ratio of alcohol and synthesis auxiliary, preference is given to determining the values given by the relationships (1) or (2) and proceeding according to the invention:

$$\frac{m_{alcohol}}{m_{HC}} = \frac{m_{alcohol-syn.} + m_{alcohol-neutr.}}{m_{HC-syn.} + m_{HC-dist.}} = \frac{x}{100-x} \quad (1)$$

In this relationship:

"$m_{alcohol-syn.}$" is the amount of alcohol generally remaining after the esterification, "$m_{alcohol-neutr.}$" is the amount of alcohol added in the neutralization with alkoxide or alcoholic alkoxide solution, "$m_{HC-syn.}$" is the amount of synthesis auxiliary which was added during the esterification, "$m_{HC\text{-}dist.}$" is the additional amount of synthesis auxiliary which may be required for the distillation and "x" is the proportion of the alcohol in the azeotrope to be distilled off in % by mass.

The additional amount of synthesis auxiliary to be added in the work-up by distillation is then advantageously:

$$m_{HC\text{-}dist.} = \frac{(m_{alcohol\text{-}syn.} + m_{alcohol\text{-}neutr.}) \cdot (100 - x)}{x} - m_{HC\text{-}syn.} \quad (2)$$

For the use of the relationships (1) and (2), reference may also be made to the examples.

In the process of the invention, the mass ratio of alcohol and synthesis auxiliary for carrying out the distillation is preferably set according to the relationship $$m_{HC\text{-}dist.} = \frac{(m_{alcohol\text{-}syn.} + m_{alcohol\text{-}neutr.}) \cdot (100 - x)}{x} - m_{HC\text{-}syn.}, \quad (2)$$

where

"$m_{alcohol\text{-}syn.}$" is the amount of alcohol generally remaining after the esterification, "$m_{alcohol\text{-}neutr.}$" is the amount of alcohol added in the neutralization with alkoxide or alcoholic alkoxide solution, "$m_{HC\text{-}syn.}$" is the amount of synthesis auxiliary which was added during the esterification, "$m_{HC\text{-}dist.}$" is the additional amount of synthesis auxiliary which may be required for the distillation and "x" is the proportion of the alcohol in the azeotrope to be distilled off in % by mass.

Compositions of possible azeotropes can generally be found in the standard literature, for example "Azeotropie Data", L. H. Horsley, (1952) American Chemical Society, Washington.

The excess alcohol can thus, according to the invention, be removed advantageously, i.e. simply and economically, from the product mixture, advantageously to leave a main fraction which comprises essentially organosilane ester of the formula I. This fraction is a composition which comprises as further components hydrocarbon including hydrocarbons of the formulae IVa, IVb or IVc and also possibly alcohol of the formula III and surprisingly gives, when applied to produce a layer or film, a layer or film having a particularly low dielectric constant, advantageously $1 < \kappa \leq 4$.

Organohalosilanes, in particular chlorosilanes, of the formula II which can be used in the process of the invention are, by way of example but not exclusively, silicon tetrachloride, methyltrichlorosilane, dimethyldichlorosilane, trimethylchlorosilane, trichlorosilane, methyldichlorosilane, dimethylchlorosilane, dichlorosilane, methylchlorosilane, triethylchlorosilane, diethyidichlorosilane, ethyltrichlorosilane, diethylchlorosilane, ethyldichlorosilane, monoethylmonochlorosilane, vinyltrichlorosilane, vinyldichlorosilane, vinylmethyldichlorosilane, vinyldimethylchlorosilane, phenyltrichlorosilane, diphenyldichlorosilane, phenylethyltrichlorosilane.

As alcohol of the formula III for the esterification, it is possible to use, for example, methanol, ethanol, n-propanol, isopropanol, n-butanol, isobutanol, tert-butanol, 2-methoxyethanol, ethoxyethanol and phenol.

According to the invention, the present process is preferably carried out using at least one synthesis auxiliary selected from the group consisting of hydrocarbons of the general formulae $C_nH_{2n+2}$ where $5 \leq n \leq 18$ (IVa)

or $C_2H_{2n}$ where $5 \leq n \leq 8$ (IVb)

or $C_nH_n$ where $4 \leq n \leq 8$ (IVc)

or corresponding alkyl-substituted cycloaliphatic or alkyl-substituted aromatic hydrocarbons or halogenated compounds of the abovementioned hydrocarbons. Thus, pentane, hexane, in particular n-hexane, heptane, octane, dodecane and isomers thereof, e.g. cyclohexane, methylcyclohexane, and mixtures of aliphatic and cycloaliphatic hydrocarbons, e.g. petroleum ether, aromatic hydrocarbons such as benzene, toluene, xylene and xylene isomers, halogenated hydrocarbons such as dichloromethane, trichloromethane and carbon tetrachloride can advantageously be used. In particular, use is made of at least one hydrocarbon which is miscible, immiscible or partially miscible with the alcohol of the formula III. However, a mixture of hydrocarbons of the formulae IVa, IVb or IVc can also be used.

In the process of the invention, preference is given to using at least one hydrocarbon which is miscible with the organosilane ester formed in the reaction.

The esterification step preferably starts from a weight ratio of halosilane: synthesis auxiliary of from 1:0.25 to 1:10, particularly preferably from 1:0.5 to 1:5, in particular about 1:1.

In the process of the invention, the reaction of the starting materials organohalosilane of the formula II and alcohol of the formula III is appropriately carried out at a temperature of from −40 to 220° C., preferably in the range from 0 to 180° C., advantageously from 40 to 150° C., particularly preferably from >60 to 120° C., very particularly preferably from 65 to 100° C., in particular from 70 to 80° C.

Furthermore, the reaction of the starting materials in the process of the invention is preferably carried out at a pressure of from 0.001 to 50 bar abs., preferably in the pressure range from 0.1 to 20 bar abs., very particularly preferably in the pressure range from 0.25 to 10 bar abs. and in particular in the pressure range from 0.5 to 1 bar abs.

Thus, the reaction in the process of the invention is preferably carried out in a homogeneous phase.

Furthermore, the distillation for working up the product mixture from the reaction in the process of the invention is appropriate carried out at a temperature at the bottom of from −40 to 220° C., preferably in the range from 0 to 140° C., particularly preferably from 20 to 85° C., with a pressure from 0.0001 to 10 bar abs. generally being set. The distillation is preferably carried out at a pressure of from 0.001 to 5 bar abs., particularly preferably at a pressure of from 0.001 to 2.5 bar abs. and very particularly preferably at a pressure of from 0.001 to 1 bar abs.

Preference is also given, in the process of the invention, to setting the mass ratio of excess alcohol to total synthesis auxiliary to a value in accordance with the relationship (1) or (2) for carrying out the distillation and if necessary regulating it to maintain it at this value.

In general, the process of the invention is carried out as follows:

As reaction vessel, it is possible to use a heatable, pressure-rated or vacuum-resistant reactor which is appropriately largely resistant to the components occurring in the reaction. Furthermore, the reactor can have, inter alia, an agitator and a facility for measuring and regulating the temperature and be connected to a distillation unit.

To carry out the reaction according to the invention, the organohalosilane, for example organochlorosilane, and the alcohol, for example methanol or ethanol, can be placed in the appropriately previously dried reactor, with the alcohol generally being used in a defined excess. It is also possible to place the organochlorosilane in the reactor and add the alcohol or vice versa.

Furthermore, a defined amount of synthesis auxiliary of the formulae IVa, IVb or IVc can be added to the reaction mixture, cf., for example, the relationships (1) and (2).

The starting materials are usually used in pure to highly pure form. The reaction can then be carried out with good mixing and temperature control. In general, the conditions for the reaction, in particular for the composition of the reaction mixture and also pressure and temperature, are set so that the reaction occurs in a homogeneous phase. During the reaction, i.e. esterification, hydrogen halide, in particular hydrogen chloride, can be removed from the system via the gas phase, for example by applying a slight to moderate vacuum or by passing advantageously water-free inert gas, e.g. nitrogen or argon, through the reactor. In addition, metal alkoxide, for example as a solution in alcohol, e.g. sodium methoxide in methanol or sodium ethoxide in ethanol, or corresponding metal alkoxide powders can be used to complete the reaction and to neutralize residual amounts of hydrogen chloride. The salt formed can be separated off, for example by filtration, and the product mixture can subsequently be worked up by distillation. For this purpose, the content of synthesis auxiliary in the product mixture is set according to the invention as a function of the alcohol content. Thus, defined amounts of synthesis auxiliary, cf., for example, the relationships (1) and (2), can also be added to the product mixture at this stage of the process.

The distillation is generally carried out as a fractional distillation in a manner known per se. Further defined amounts of synthesis auxiliary can also be added during the distillation. Thus, it can be advantageous firstly to remove alcohol or synthesis auxiliary or azeotrope from the system before the organosilane ester fraction is taken off. In addition, a composition which is rich in organosilane ester and comprises, in addition to the organosilane ester, defined amounts of hydrocarbon of the formulae IVa, IVb or IVc and possibly defined amounts of alcohol of the formula III can advantageously be obtained in the manner described.

Thus, organosilane esters of the formula I, for example methyltrimethoxysilane, dimethyldimethoxysilane, dimethyldiethoxysilane, trimethylmethoxysilane, trimethylethoxysilane, trimethoxysilane, triethoxysilane, methyldimethoxysilane, methyldiethoxysilane, dimethylmethoxysilane, dimethylethoxysilane, dimethoxysilane, diethoxysilane, methylmethoxysilane, methylethoxysilane, triethylmethoxysilane, triethylethoxysilane, dimethyldimethoxysilane, diethyldiethoxysilane, ethyltrimethoxysilane, ethyltriethoxysilane, diethylmethoxysilane, diethylethoxysilane, ethyldimethoxysilane, ethyldiethoxysilane, ethylmethoxysilane, ethylethoxysilane, vinyldimethoxysilane, vinyldiethoxysilane, vinylmethyldimethoxysilane, vinylmethyldiethoxysilane, vinylmethyldimethoxysilane, vinyldimethylethoxysilane, to name only a few, can be prepared in a comparatively simple and economical way by the process of the invention.

The present invention further provides a process for preparing a composition comprising more than 98% by weight of organosilane ester of the formula I and less than 2% by weight of hydrocarbons of at least one of the formulae IVa, IVb and IVc, in each case based on the total composition, by carrying out the process as claimed in any of claims 1 to 9 and discharging the fraction comprising more than 98% by weight of organosilane ester in the fractional distillation.

The present invention likewise provides a composition comprising more than 98% by weight of an organosilane ester of the formula I and less than 2.0% by weight of at least one hydrocarbon of at least one of the formulae IVa, IVb and IVc, in each case based on the total composition, obtainable as claimed in claim 10.

The present invention therefore also provides a composition consisting of more than 98% by weight of organosilane ester of the formula I and less than 2.0% by weight of at least one hydrocarbon, based on the total composition, with the sum of the components of the composition being 100% by weight.

In particular, the composition of the invention has a proportional content of an organosilane ester of from 99.0 to 99.99% by weight, particularly preferably from 99.4 to 99.95% by weight, very particularly preferably from 99.6 to 99.9% by weight.

The composition of the invention also preferably has a proportional content of hydrocarbons of from 0.001 to 1.5% by weight, particularly preferably from 0.005 to 1% by weight, very particularly preferably from 0.05 to 0.5% by weight, in particular from 0.01 to 0.2% by weight.

The composition of the invention can likewise have a proportional content of an alcohol, preferably an alcohol corresponding to the alkoxide of the silane ester, of from 0.0001 to 0.5% by weight, particularly preferably from 0.0005 to 0.2% by weight, very particularly preferably from 0.001 to 0.1% by weight.

In addition, the present invention provides for the use of a composition according to the invention as precursor for producing a layer having a dielectric constant of $1<\kappa\leq 4$, particularly preferably $1.5 \leq \kappa \leq 3.5$, very particularly preferably $1.8 \leq \kappa \leq 2.8$.

Thus, the composition of the invention can be used, by way of example but not exclusively, as precursors or vaporizable, silicon-containing starting materials in film forming processes which operate according to the CVD or spin-on method.

CVD Method:

Here, precursors based on silicon or mixtures of precursors are usually vaporized in suitable reactors, e.g. Applied Centura HAT, Novellus Concept One 200 or ASM Eagle-10, and are allowed to react on hot surfaces, e.g. a silicon wafer, to form a layer of solid material. Further developments of this method, for example RPCVD (reduced pressure chemical vapor deposition), LPCVD (low pressure chemical vapor deposition) and PECVD (plasma enhanced chemical vapor deposition), which make more rapid deposition at sometimes significantly reduced temperatures possible, have also been found to be advantageous.

Spin-On Method:

In this method, liquid silicon-containing compounds, mixtures of liquid silicon-containing compounds, solutions of silicon-containing compounds in suitable vaporizable solvents or solutions of silicon-containing compounds in suitable vaporizable solvents or decomposable, pore-forming substances, e.g. compositions comprising organic polymers such as POM, PMMA, PEO, PPO, are placed on the surface of a silicon wafer and a uniform thin film is produced by rotation of the wafer. In general, the film produced in this way is cured by means of a subsequent thermal treatment at from 20 to 500° C.

The present invention is illustrated by the following examples, without restricting its scope.

EXAMPLES

Examples A and B below illustrate the use of the relationships (1) and (2):

Example A

Esterification of a Chlorosilane by Means of Ethanol in Cyclohexane:

The azeotrope to be distilled off boils at about 65° C. and appropriately contains 30.5% by mass of ethanol (x=30.5).

After neutralization with ethanolic sodium ethoxide solution, 175 g of ethanol, for example, are present in the product mixture ($m_{alcohol\text{-}syn.}+m_{alcohol\text{-}neutr.}=175$ g). The esterification was carried out in 300 g of cyclohexane ($m_{HC\text{-}syn.}=300$ g).

The amount of additional cyclohexane required for carrying out the distillation according to the invention is given by (2) as:

$$m_{cyclohexane\text{-}dist.} = \frac{175 \text{ g} \cdot (100 - 30.5)}{30.5} - 300 \text{ g} = 98.8 \text{ g}$$

In the present case, an amount of cyclohexane of 398.8 g is to be set in the initial charge for carrying out the distillation.

Example B

Esterification of a Chlorosilane by Means of Methanol in n-hexane:

The azeotrope to be distilled off boils at about 49° C. and contains 29.8% by mass of methanol.

After neutralization with methanolic sodium methoxide solution, 147 g of methanol are present in the product mixture. The esterification was carried out in 250 g of n-hexane.

The amount of additional n-hexane required for carrying out the distillation is given by (2) as:

$$m_{n\text{-}hexane\text{-}dist.} = \frac{147 \text{ g} \cdot (100 - 29.8)}{29.8} - 250 \text{ g} = 96.3 \text{ g}$$

Example 1 (Comparative Example)

500 g of dimethyldichlorosilane are placed in a four-neck flask provided with reflux condenser, mechanical stirrer, thermometer and a Teflon feed line. While stirring continually, 186 g of methanol are metered in at 40-50° C. over a period of 5 hours. Due to commencement of oligomerization, the mixture is neutralized with 466 g of sodium methoxide solution (30% in methanol) and the esterification is completed. The salt formed is filtered off and the filtrate (829 g) is subjected to a fractional distillation. The distillation is carried out at atmospheric pressure via a glass column packed with ceramic bodies and having an effective height of 75 cm and a temperature of the bottom heating of 100° C. The final fraction is distilled off by reducing the pressure to 150 mbar.

The results of the distillation are shown in Table 1.

TABLE 1

| Fraction | Mass (g) | Boiling point p (° C.) | GC-WLD (%) | | |
|---|---|---|---|---|---|
| | | | Methanol | DMDMO* | Oligomers |
| 1 | 125 | 61 | 38.0 | 61.4 | 0.6 |
| 2 | 179 | 62 | 40.4 | 59.4 | 0.2 |
| 3 | 200 | 62 | 38.2 | 61.9 | — |
| 4 | 277 | 64 | 67.9 | 32.1 | 0.1 |
| Final fraction | 20 | ~62 | 95.9 | 4.0 | 0.1 |
| Residue | 28 | | 48.1 | 1.2 | 50.8 |

* = Dimethyldimethoxysilane

Table 1 shows that separation into the pure components by distillation is not possible.

Methanol obviously forms an azeotrope with dimethyldimethoxysilane which boils at 62° C. and has a composition of about 40 GC-% by area of methanol and about 60 GC-% by area of dimethyidimethoxysilane.

Example 2

500 g of dimethyldichlorosilane are placed in a four-neck flask provided with reflux condenser, mechanical stirrer, thermometer and a Teflon feed line. While stirring continually, 186 g of methanol are metered in at 40-50° C. over a period of 5 hours. Due to commencement of oligomerization, the mixture is neutralized with 466 g of sodium methoxide solution (30% in methanol) and the esterification is completed. The salt formed is filtered off and 1082 g of n-hexane are added to the filtrate (829 g). This mixture is subjected to a fractional distillation. The distillation is carried out at atmospheric pressure via a glass column packed with ceramic bodies and having an effective height of 75 cm and a temperature of the bottom heating of 100° C. The final fraction is distilled off by reducing the pressure to 150 mbar.

The results of the distillation are shown in Table 2.

TABLE 2

| Fraction | Mass (g) | Boiling point p (° C.) | GC-WLD (%) | | | |
|---|---|---|---|---|---|---|
| | | | Hexane | Methanol | DMDMO* | Oligomers |
| 1 | 93 | 50 | 80.7 | 19.2 | 0.1 | — |
| 2 | 277 | 49 | 76.2 | 23.8 | — | — |
| 3 | 304 | 49 | 72.1 | 27.9 | — | — |
| 4 | 323 | 49 | 72.2 | 27.7 | — | — |
| 5 | 82 | 49 | 74.5 | 25.5 | — | — |
| 6 | 311 | 49 | 74.0 | 26.0 | — | — |
| 7 | 39 | 49 | 67.3 | 32.7 | — | — |
| 8 | 43 | 67 | 72.3 | 25.7 | 2.0 | — |
| 9 | 38 | 71 | 67.1 | 0.6 | 32.3 | — |
| 10 | 25 | 80 | 39.2 | 0.1 | 60.7 | — |
| 11 | 19 | 81 | 6.9 | 0.1 | 93.0 | — |
| 12 | 43 | 81 | 1.7 | — | 98.3 | — |
| 13 | 208 | 81 | 1.4 | — | 98.6 | — |
| Final fraction | 54 | ~69 | 3.0 | — | 94.5 | 2.5 |
| Residue | 4 | — | 1.6 | 0.7 | 43.6 | 54.1 |

* =Dimethyldimethoxysilane

As can be seen from Table 2, separation of methanol and DMDMO by distillation is possible after addition of n-hexane, and azeotrope formation is overcome thereby.

Example 3

500 g of dimethyldichlorosilane together with 500 g of n-hexane are placed in a four-neck flask provided with reflux condenser, mechanical stirrer, thermometer and a Teflon feed line. While stirring continually, 248 g of methanol are metered in at 45-55° C. over a period of 5 hours. The mixture is subsequently neutralized with 259 g of sodium methoxide solution (30% in methanol). The salt formed is filtered off, 292 g of n-hexane are added and the filtrate (1424 g) is subjected to a fractional distillation, parameters as in Example 2. The distillation is carried out at atmospheric pressure via a packed column (ceramic) (oil bath temperature: 100° C.). The final fraction is distilled off by reducing the pressure to 150 mbar.

The results of the distillation are shown in Table 3.

TABLE 3

| Fraction | Mass (g) | Boiling point p (° C.) | GC-WLD (%) | | | |
|---|---|---|---|---|---|---|
| | | | Hexane | Methanol | DMDMO* | Oligomers |
| 1 | 84 | 49 | 71.4 | 28.6 | — | — |
| 2 | 350 | 49 | 72.0 | 27.9 | — | — |
| 3 | 197 | 50 | 75.4 | 23.5 | — | — |
| 4 | 264 | 50 | 72.7 | 27.3 | — | — |
| 5 | 64 | 69 | 76.9 | 4.1 | 19.0 | — |
| 6 | 65 | 79 | 58.5 | 0.1 | 41.4 | — |
| 7 | 48 | 81 | 7.0 | — | 92.9 | — |
| 8 | 258 | 81 | 0.8 | — | 99.2 | — |
| Final fraction | 83 | ~72 | 1.6 | — | 98.4 | — |
| Residue | 11 | — | 1.2 | 3.9 | 33.6 | 61.3 |

* = Dimethyldimethoxysilane

Example 3 shows that the addition of n-hexane as early as during the reaction of the starting materials is advantageous. The highest yield of DMDMO at the lowest consumption of sodium methoxide is obtained in this way. This means an n-hexane-influenced reaction and distillation has a positive effect on the formation and isolation in pure form of DMDMO.

Example 4

500 g of dimethyldichlorosilane are placed in a four-neck flask provided with reflux condenser, mechanical stirrer, thermometer and a Teflon feed line. While stirring continually, 845 g of the methanol/n-hexane first fraction distilled off in Example 2 are metered in at 45-55° C. over a period of 5.5 hours. The mixture is subsequently neutralized with 279.5 g of sodium methoxide solution (30% in methanol). The salt formed is filtered off. After completion of the work-up, 306 g of DMDMO are obtained. Example 4 shows that the first fraction can be recirculated to the reaction.

Example 5

1000 g of dimethyldichlorosilane together with 945 g of n-hexane are placed in a four-neck flask provided with reflux condenser, mechanical stirrer, thermometer and a Teflon feed line. While stirring continually, 496 g of methanol are metered in at 45-55° C. over a period of 5.5 hours. The mixture is subsequently neutralized with 475 g of sodium methoxide solution (30% in methanol). The salt formed is filtered off and 1989 g of filtrate are obtained. 1372 g of the filtrate are subjected to a fractional distillation. The distillation is carried out at atmospheric pressure via a 110 cm column provided with metal mesh packing (oil bath temperature: 80-120° C.). 860 g of the hexane-rich phases of the fractions 1 to 3 distilled off are in each case poured back into the distillation pot after taking off the fraction.

Result of the Distillation:

| Fraction | Mass (g) | Bp. (° C.) p | GC-WLD (%) | | | |
|---|---|---|---|---|---|---|
| | | | Hexane | Methanol | DMDMO* | Oligomers |
| 1 | 628 | 49 | 73.5 | 26.5 | — | — |
| 2 | 341 | 49 | 73.5 | 26.5 | — | — |
| 3 | 303 | 50 | 73.4 | 26.6 | — | — |
| 4 | 125 | 50 | 77.5 | 22.5 | — | — |
| 5 | 79 | 50 | 74.1 | 22.1 | 2.5 | — |
| 6 | 64 | 79 | 88.9 | 0.1 | 10.0 | — |
| 7 | 266 | 81 | 80.2 | — | 18.8 | — |
| 8 | 51 | 82 | 0.4 | 0.1 | 99.4 | — |
| 9 | 313 | 82 | — | — | 99.95 | — |
| 10 | 9 | 82 | — | — | 99.92 | — |
| Residue | 49 | — | — | — | 81.6 | 18.4 |

* Dimethyldimethoxysilan

Example 5 shows that DMDMO of very high purity as is required, in particular, in the electronic applications mentioned can be obtained by the process.

The invention claimed is:

1. A process for preparing a composition, comprising:
carrying out a process for preparing organosilane esters of the general formula I $$R^1_a R^2_b R^3_c Si(OR^4)_{4-a-b-c} \quad (I),$$

wherein $R^1$=hydrogen, alkyl or aryl, $R^2$=hydrogen or alkyl, $R^3$=hydrogen or alkyl and $R^4$=alkyl, aryl or alkoxyalkyl, a, b and c can be identical or different and can each be 0, 1, 2 or 3, with the proviso that $(a+b+c)\leq 3$,
by reacting an organohalosilane of the general formula II $$R^1_a R^2_b R^3_c SiX_{4-a-b-c} \quad (II),$$

wherein $R^1$=hydrogen, alkyl, alkenyl or aryl, $R^2$=hydrogen or alkyl, $R^3$=hydrogen or alkyl and $R^4$=alkyl, aryl or alkoxyalkyl, X is fluorine, chlorine, bromine or iodine, a, b and c can be identical or different and can each be 0, 1, 2 or 3, with the proviso that $(a+b+c)\leq 3$,
with an alcohol of the general formula III $$R^4OH \quad (III)$$

wherein $R^4$=alkyl, aryl or alkoxyalkyl,
wherein
the halosilane is reacted in the liquid phase with the alcohol in the presence or absence of at least one synthesis auxiliary,
hydrogen halide is removed from the system,
optionally, metal alkoxide is added to the reaction mixture and the metal salt formed is filtered off, and
an amount of synthesis auxiliary is added at least once before or during the subsequent work-up by distillation of the resulting product mixture, with the amount added in each case being such that no azeotrope of one or more components of the product mixture and the organosilane ester of the formula I is formed during the distillation under the conditions which prevail;

wherein said synthesis auxiliary is at least one member selected from the group consisting of hydrocarbons of the general formulae $C_nH_{2n+2}$ with $5 \leq n \leq 18$, (IVa)

$C_2H_{2n}$ with $5 \leq n \leq 8$, (IVb)

$C_nH_n$ with $4 \leq n \leq 8$, (IVc)

corresponding alkyl-substituted cycloaliphatic, alkyl-substituted aromatic hydrocarbons, halogenated compounds of the abovementioned hydrocarbons and mixtures thereof; and discharging a fraction comprising more than 98% by weight of organosilane ester in the fractional distillation, to obtain a composition comprising:

more than 98% by weight of organosilane ester of the formula I and less than 2% and more than 0% by weight of hydrocarbons of at least one of the formulae IVa, IVb and IVc, in each case based on the total composition.

2. The process as claimed in claim 1, wherein at least one hydrocarbon which is miscible, immiscible or partially miscible with the alcohol of the formula III is used.

3. The process as claimed in claim 1, wherein at least one hydrocarbon which is miscible with the organosilane ester formed in the reaction is used.

4. The process as claimed in claim 1, wherein the reaction of the starting materials organohalosilane of the formula II and alcohol of the formula III is carried out at a temperature of from −40 to 220° C.

5. The process as claimed in claim 1, wherein the reaction of the starting materials is carried out at a pressure in the range from 0.001 to 50 bar abs.

6. The process as claimed in claim 1, wherein the distillation for working up the product mixture from the reaction is carried out at a temperature at the bottom of from −40 to 220° C.

7. The process as claimed in claim 1, wherein the reaction is carried out in a homogeneous phase.

8. The process as claimed in claim 1, wherein the mass ratio of alcohol to synthesis auxiliary for carrying out the distillation is set according to the relationship $$m_{HC-dist.} = \frac{(m_{alcohol-syn.} + m_{alcohol-neutr.}) \cdot (100 - x)}{x} - m_{HC-syn.}, \quad (2)$$

where

"$m_{alcohol-syn.}$" is the amount of alcohol remaining after the esterification, "$m_{alcohol-neutr.}$" is the amount of alcohol added in the neutralization with alkoxide or alcoholic alkoxide solution, "$m_{HC-syn.}$" is the amount of synthesis auxiliary which was added during the esterification, "$m_{HC-dist.}$" is the additional amount of synthesis auxiliary which may be required for the distillation and "x" is the proportion of the alcohol in the azeotrope to be distilled off in % by mass.

9. A composition obtained by the process of claim 1, said composition comprising:

more than 98% by weight of an organosilane ester of the formula I, and less than 2.0% and more than 0% by weight of at least one hydrocarbon of at least one of the formulae IVa, IVb and IVc, in each case based on the total composition.

10. The composition as claimed in claim 9 having a hydrocarbon content of from 0.001 to 1.5% by weight.

11. The composition as claimed in claim 9 having a content of an organosilane ester of from 99.0 to 99.99% by weight.

12. The composition as claimed in claim 9 having a content of an alcohol of from 0.0001 to 0.5% by weight.

13. A composition comprising more than 98% by weight of organosilane esters of the formula I $$R^1_aR^2_bR^3_cSi(OR^4)_{4-a-b-c} \quad (I),$$

wherein $R^1$=hydrogen, alkyl or aryl, $R^2$=hydrogen or alkyl, $R^3$=hydrogen or alkyl and $R^4$=alkyl, aryl or alkoxyalkyl, a, b and c can be identical or different and can each be 0, 1, 2 or 3, with the proviso that $(a+b+c) \leq 3$; and less than 2.0% by weight and more than 0% of at least one hydrocarbon of the formula IVa, IVb or IVc, based on the total composition;

wherein formula IVa is $C_nH_{2n+2}$ with $5 \leq n \leq 18$;

wherein formula IVb is $C_2H_{2n}$ with $5 \leq n \leq 8$; and wherein formula IVc is $C_nH_n$ with $4 \leq n \leq 8$.

14. A composition for producing a layer or film having a dielectric constant of $1 < \kappa \leq 4$, said composition comprising the composition as claimed in claim 13.

15. A composition for producing a layer or film having a dielectric constant of $1 < \kappa \leq 4$, said composition comprising the composition as claimed in claim 9.

* * * * *